US008389788B2

(12) United States Patent
Taoufik et al.

(10) Patent No.: US 8,389,788 B2
(45) Date of Patent: Mar. 5, 2013

(54) OLEFIN METATHESIS REACTANT RATIOS USED WITH TUNGSTEN HYDRIDE CATALYSTS

(75) Inventors: Mostafa Taoufik, Villeurbanne (FR); Etienne Mazoyer, Lyons (FR); Christopher P. Nicholas, Evanston, IL (US); Jean-Marie Basset, Caluire (FR)

(73) Assignee: UOP LLC, Des Plaines, IL (US)

( * ) Notice: Subject to any disclaimer, the term of this patent is extended or adjusted under 35 U.S.C. 154(b) by 326 days.

(21) Appl. No.: 12/749,937

(22) Filed: Mar. 30, 2010

(65) Prior Publication Data

US 2011/0245560 A1  Oct. 6, 2011

(51) Int. Cl.
C07C 6/02 (2006.01)
(52) U.S. Cl. ........................................ 585/646; 585/643
(58) Field of Classification Search .................. 585/643, 585/646
See application file for complete search history.

(56) References Cited

U.S. PATENT DOCUMENTS

| | | | |
|---|---|---|---|
| 3,691,095 A * | 9/1972 | Kroll et al. .................... 502/102 |
| 3,978,150 A | 8/1976 | McWilliams, Jr. | |
| 4,575,575 A | 3/1986 | Drake et al. | |
| 4,754,098 A | 6/1988 | Drake | |
| 5,296,437 A | 3/1994 | Hietala et al. | |
| 5,300,718 A | 4/1994 | McCaulley et al. | |
| 5,914,433 A | 6/1999 | Marker | |
| 6,388,161 B1 | 5/2002 | Dath et al. | |
| 6,420,619 B1 | 7/2002 | Gartside et al. | |
| 6,858,133 B2 | 2/2005 | Dath et al. | |
| 6,867,341 B1 | 3/2005 | Abrevaya et al. | |
| 7,087,155 B1 | 8/2006 | Dath et al. | |
| 7,214,841 B2 | 5/2007 | Gartside et al. | |
| 7,268,265 B1 | 9/2007 | Stewart et al. | |
| 7,375,257 B2 | 5/2008 | Dath et al. | |
| 7,586,018 B2 | 9/2009 | Bozzano et al. | |
| 2005/0124839 A1* | 6/2005 | Gartside et al. ............... 585/643 |
| 2007/0129584 A1 | 6/2007 | Basset et al. | |
| 2007/0203384 A1 | 8/2007 | Pujado et al. | |
| 2008/0081936 A1 | 4/2008 | Bozzano et al. | |
| 2008/0228020 A1* | 9/2008 | Coperet et al. ................ 585/502 |
| 2008/0255328 A1* | 10/2008 | Basset et al. ................... 526/154 |
| 2010/0056839 A1 | 3/2010 | Ramachandran et al. | |

OTHER PUBLICATIONS

Taoufik, et al., "Direct Transformation of Ethylene into Propylene Catalyzed by as Tungsten Hydride Supported on Alumina: Trifunctional Single-Site Catalysis" in Angew. Chem. Int. Ed., 2007, 46, 7202-7205.—2007, month unknown.*
Sundaram, et al., "Ethylene" in Kirk-Othmer Encyclopedia of Chemical Technology, John Wiley & Sons, 2001, available on-line Apr. 16, 2001.*
Leofanti, et al., "Surface Area and Pore Texture of Catalysts" in Catalysis Today, 41, 1998, 207-219.—1998, month uknown.*
Chodorge, J.A. et al., "Propylene production from butenes and ethylene," Petroleum Technology Quarterly. Crambeth Allen Publishing (ISSN 1362-363) pp. 109-10, 112, 114-15 (Spring 1997).

(Continued)

Primary Examiner — In Suk Bullock
Assistant Examiner — Bradley Etherton
(74) Attorney, Agent, or Firm — Arthur E. Gooding

(57) ABSTRACT

Processes for olefin metathesis, for example for the production of propylene, utilize a catalyst comprising a solid support and a tungsten hydride bonded to alumina present in the support. Conversion, selectivity, and/or catalyst stability advantages may be realized when a first olefin reactant (e.g., ethylene) is present in the hydrocarbon feedstock at a stoichiometric deficit relative to a second, higher carbon number olefin reactant (e.g., butylene).

19 Claims, 4 Drawing Sheets

OTHER PUBLICATIONS

Dai, W. et al., "Review of propylene production through olefins conversion," Petrochemical Technology. 37(5): 425-433, Beijing Research Institute of Chemical Industry, Language: Chinese [Abstract] (2008).

Cosyns, Jr. "Achennasia '98: Petrochemical developments/Maximize propylene production," Hydrocarbon Processing. Gulf Publishing Co. (ISSN 0018-8190) 77(3): 61-66 (Mar. 1998).

Gomes, V.G. et al., "A periodic separating reactor for propene metathesis," Chemical Engineering Science 57(18): 3839-3850 (2002).

PCT International Search and Written Opinion for PCT/US2011/030287, mailing date Dec. 19, 2011.

* cited by examiner

US 8,389,788 B2

OLEFIN METATHESIS REACTANT RATIOS USED WITH TUNGSTEN HYDRIDE CATALYSTS

FIELD OF THE INVENTION

The invention relates to processes for the metathesis of olefins, for example in the production of propylene from olefin feedstocks comprising ethylene and butylene at a stoichiometric deficit of the former. A representative catalyst comprises a tungsten hydride bonded to alumina that is present in the support.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. Nos. 5,026,935 and 5,026,936. The cracking of olefins in hydrocarbon feedstocks, to produce these lighter olefins from $C_4$ mixtures obtained in refineries and steam cracking units, is described in U.S. Pat. Nos. 6,858,133; 7,087,155; and 7,375,257.

Steam cracking, whether or not combined with conventional metathesis and/or olefin cracking steps, does not yield sufficient propylene to satisfy worldwide demand. Other significant sources of propylene are therefore required. These sources include byproducts of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ byproduct stream of FCC may be purified in propylene to polymer grade specifications by the separation of $C_4$ hydrocarbons, propane, ethane, and other compounds.

Much of the current propylene production is therefore not "on purpose," but as a byproduct of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

The invention is associated with the discovery of processes for olefin metathesis, including those for the production of valuable light olefins such as propylene. More particularly, it has been surprisingly discovered that carrying out olefin metathesis with a particular catalyst system and under particular olefin reactant ratios effectively improves the activity of the resulting catalyst (i.e., its conversion level at a given temperature) for the metathesis of olefins, without significantly compromising its selectivity to the desired olefin product(s). In fact, the use of a catalyst comprising a tungsten hydride that is bonded to alumina present in the catalyst support exhibits unexpected increases in both conversion and selectivity, under olefin metathesis conditions, as the molar ratio of olefin reactants shifts away from the stoichiometric reaction ratio, and particularly in the direction such that a first olefin reactant is in a stoichiometric deficit relative to a second olefin reactant, having a carbon number of at least two greater than that of the first olefin reactant. This contrasts significantly with other olefin metathesis catalyst systems operating at the stoichiometric reaction ratio or even with a stoichiometric excess of the first olefin reactant. For example, total reactant conversion based on carbon, at a molar ratio of the first olefin to the second olefin in a range from about 0.2:1 to less than 1:1, can exceed the conversion level obtained when the ratio is 1:1 or greater. Yet a further benefit of carrying out the olefin metathesis in this manner is an increase in catalyst stability.

These experimental findings with respect to tungsten hydride catalysts would not have been predictable, in view of the normal expectations that (i) equimolar reactant concentrations should lead to the most efficient conversion of carbon in the olefin reactants, in processes such as olefin metathesis involving a 1 to 1 molar ratio of these reactants and (ii) greater conversion levels are obtained at the expense of a loss in selectivity. Typical olefin metathesis processes for the production of propylene are conventionally operated, for example, at a 1:1 molar ratio of ethylene:butylene or even with a molar excess of ethylene in an attempt to increase propylene selectivity.

Without being bound by theory, it is thought that these unexpected benefits result from activation/stabilization effects due to the second, higher carbon number olefin reactant being present in the metathesis reaction environment at a concentration that is relatively higher than that of the first, lower carbon number olefin reactant. Greater catalyst activation and stabilization characteristics of the second olefin reactant, and particularly with the tungsten hydride/alumina catalyst system, is thought to promote the more efficient utilization of carbon in the hydrocarbon feedstock for conversion to the desired product (e.g., propylene), such that the selectivity of the metathesis reaction to this desired product is maintained even at higher conversion levels, thereby increasing its yield while simultaneously improving catalyst stability.

Increased olefin metathesis activity may be exploited commercially by reducing the requirement to heat the olefin-containing hydrocarbon feedstock, prior to its contact with the catalyst at the inlet of the olefin metathesis reaction zone. Alternatively, increased product yield (the product of conversion and selectivity) may be obtained at a given reactor temperature. It will be recognized that cost advantages, associated with decreased energy requirements and/or greater product value, result in either case. In view of the current demand for propylene, it will be appreciated that even a slight improvement in product yield, on the order of only a few percent, can result in substantial economic advantages, on the order of several million dollars per year in increased product value, for a typical petrochemical producer. The improved value of the product slate is accompanied by a reduction in downstream separation requirements for removing non-selective reaction products (e.g., $C_5^+$ olefins), and also a reduction in equipment and utilities required for the recycle of unconverted olefin reactants. Moreover, improvements in catalyst stability prolong useful catalyst life, providing additional cost advantages in terms of material savings.

Accordingly, embodiments of the invention relate to olefin metathesis processes comprising contacting a hydrocarbon feedstock with a catalyst comprising a solid support and a tungsten hydride bonded to alumina present in the support. The hydrocarbon feedstock comprises olefins including a first olefin (e.g., ethylene) and a second olefin (e.g., butylene) having a carbon number of at least two greater than that of the first olefin, to produce a third olefin (e.g., propylene) having a carbon number intermediate to the first and second olefins. Advantageously, the first olefin is at a stoichiometric deficit relative to the second olefin. In particular embodiments, for example, a molar ratio of the first olefin to the second olefin in the hydrocarbon feedstock is in a range from about 0.2:1 to less than 1:1, and is often in a range from about 0.4:1 to about 0.8:1.

More particular embodiments of the invention relate to processes for producing propylene from the metathesis of ethylene and butylene. The processes comprise contacting a hydrocarbon feedstock comprising predominantly ethylene and butylene at an ethylene:butylene molar ratio from about 0.4:1 to about 0.8:1 with a catalyst comprising a solid support and a tungsten hydride bonded to alumina present in the support. A per pass conversion according to this embodiment is from about 30% to about 65% based on carbon, and the ethylene and butylene are converted to propylene with a selectivity of at least about 80% based on carbon. According to any of the above embodiments, the catalyst may comprise tungsten in an amount from about 1% to about 10% by weight and the support may have a surface area surface area from about 100 m²/g to about 450 m²/g.

These and other aspects and embodiments associated with the present invention are apparent from the following Detailed Description.

Figure 1:
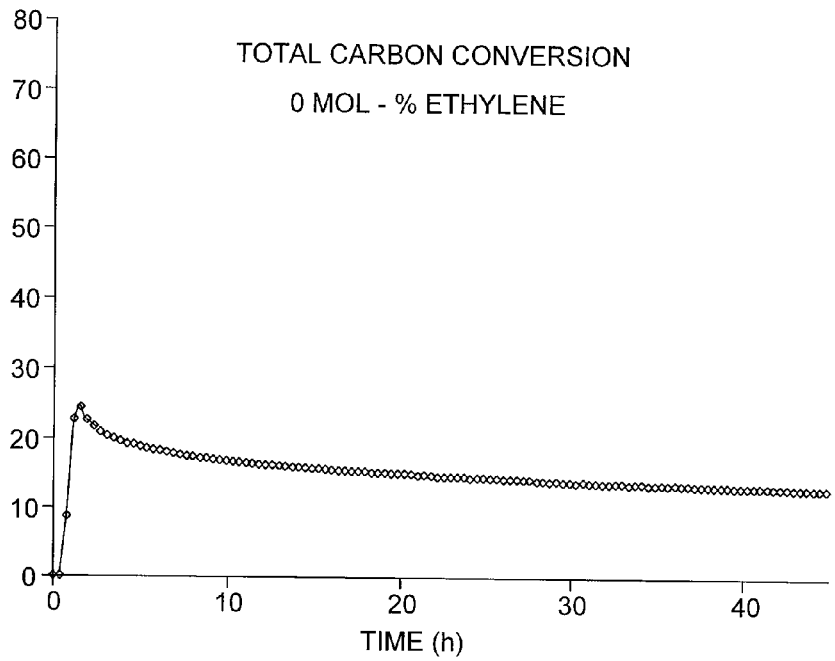
FIGS. 1-7 are graphs showing the (i) conversion of ethylene, (ii) conversion of butylene, and (iii) conversion of total carbon in the ethylene and butylene reactants, as a function of time on stream. The conversion data were obtained in the production of propylene from feedstocks with ethylene/butylene in molar amounts of 0%/100% (FIG. 1), 10%/90% (FIG. 2), 18%/82% (FIG. 3), 35%/65% (FIG. 4), 45%/55% (FIG. 5), 70%/30% (FIG. 6), and 100%/0% (FIG. 7).
Figure 2:
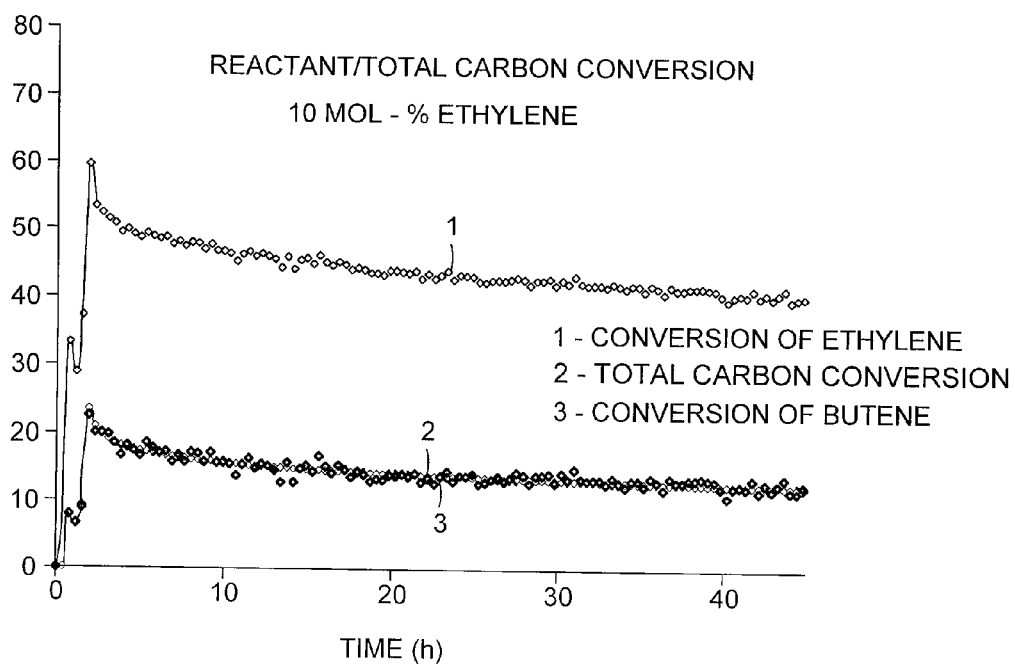
Figure 3:
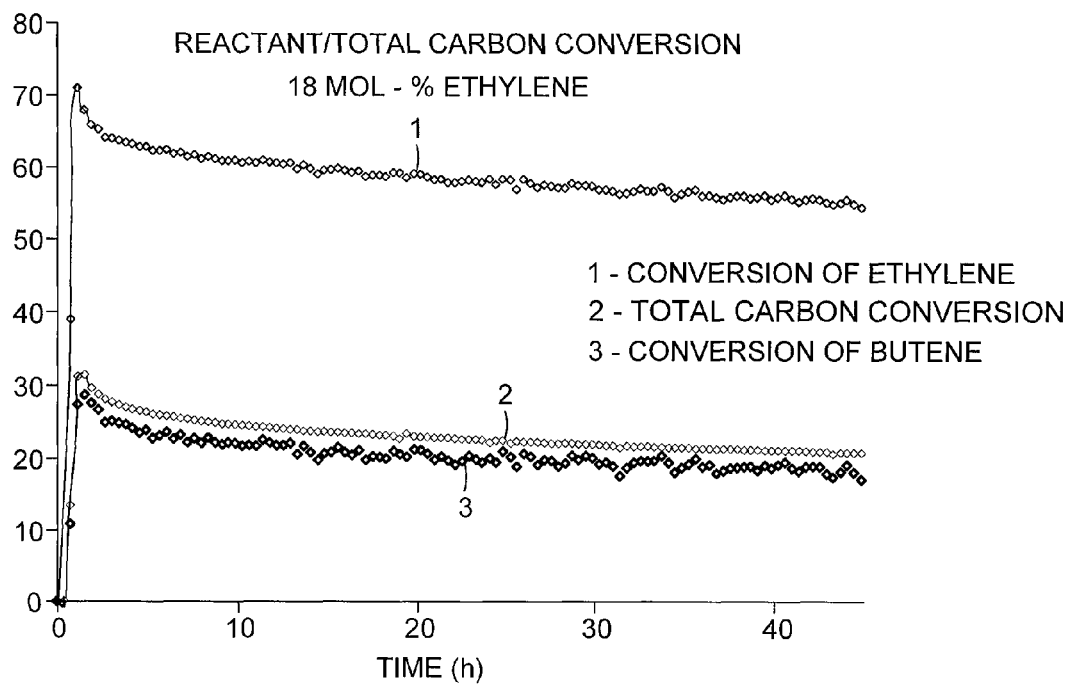
Figure 4:
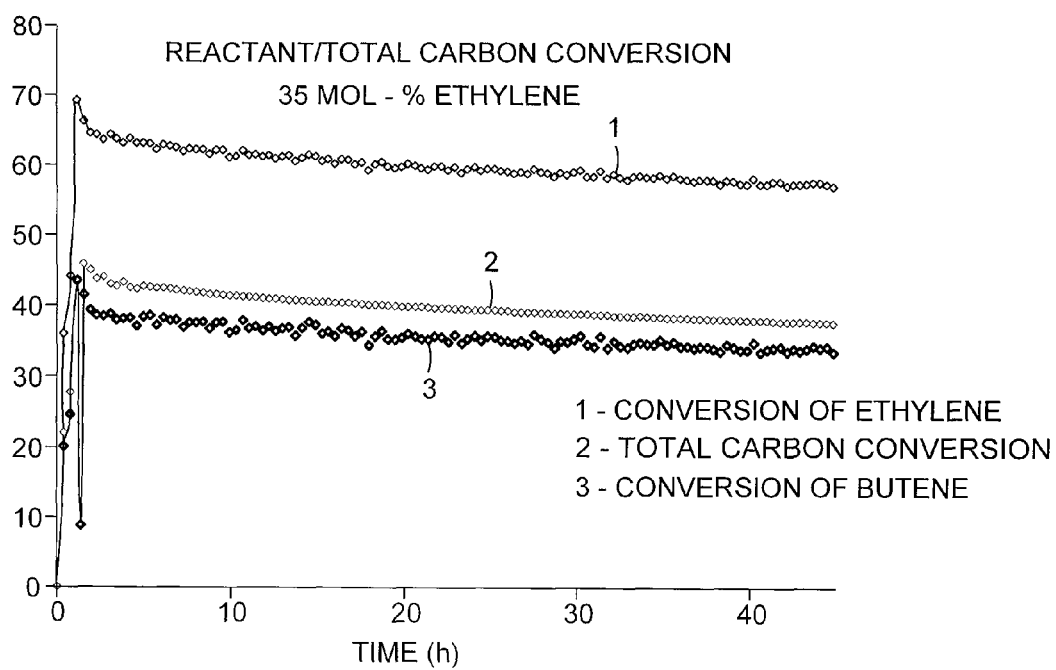
Figure 5:
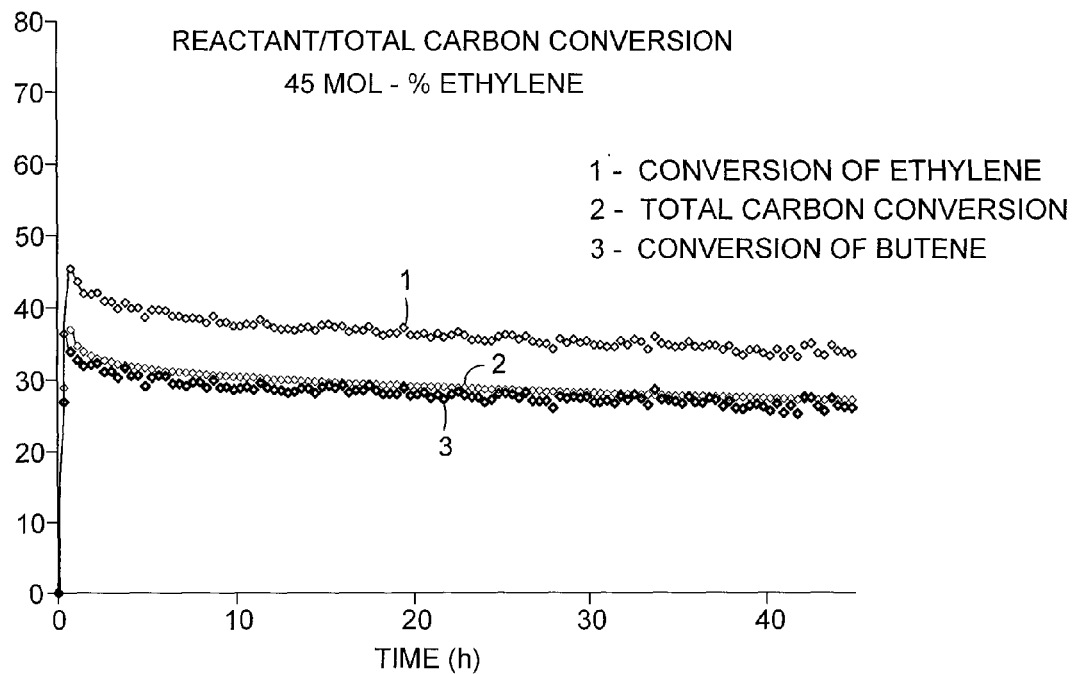
Figure 6:
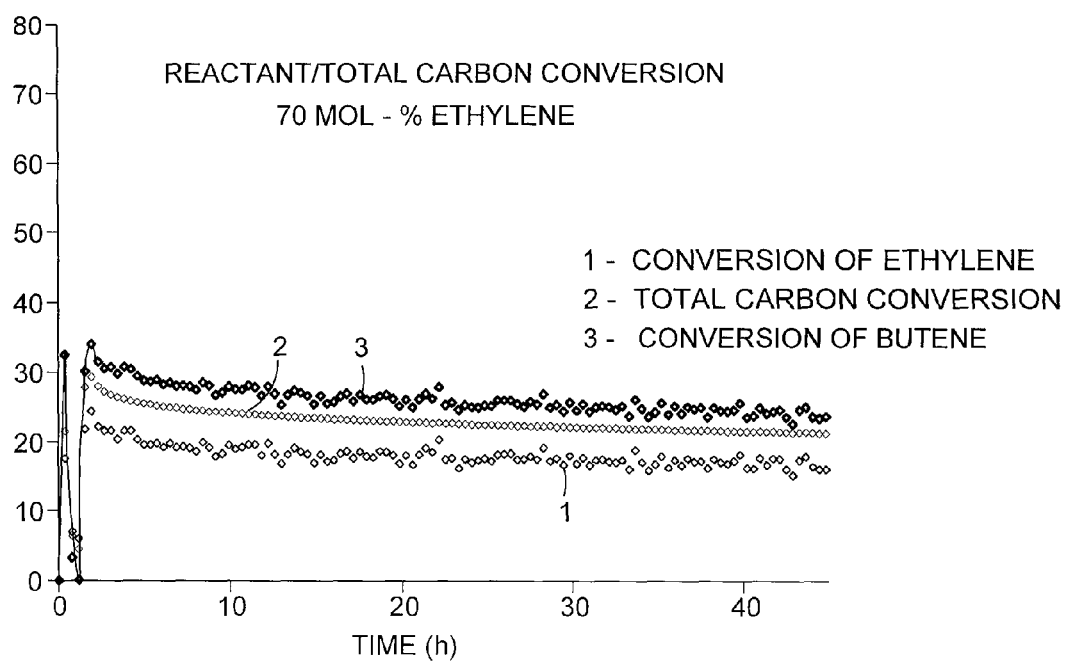
Figure 7:
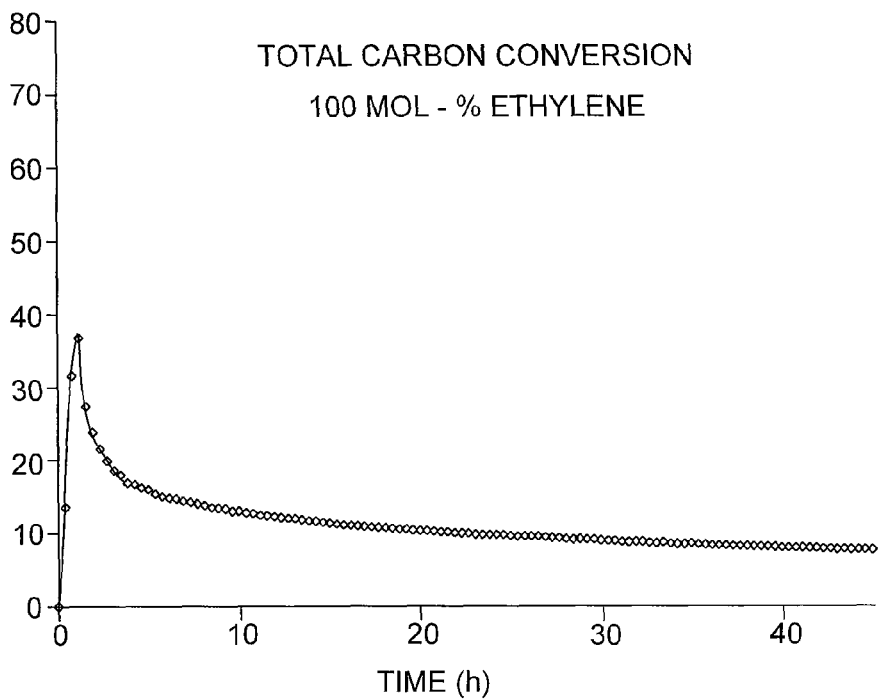

The catalyst used to obtain the data presented in FIGS. 1-8 was a catalyst comprising a tungsten hydride bonded to alumina present in the support.

DETAILED DESCRIPTION

As discussed above, the present invention is associated with catalytic olefin metathesis (or disproportionation) processes in which a hydrocarbon feedstock is contacted, in a metathesis reactor or reaction zone, with a catalyst comprising a solid support and a tungsten hydride bonded to alumina present in the support. The hydrocarbon feedstock refers to the total, combined feed, including any recycle hydrocarbon streams, to the catalyst in the metathesis reactor or reaction zone, but not including any non-hydrocarbon gaseous diluents (e.g., nitrogen), which may be added according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in olefin metathesis processes according to the present invention, the hydrocarbons contained in the hydrocarbon feedstock are generally predominantly (i.e., at least 50% by weight, such as from about 60% to about 100% by weight) olefins, typically they comprise at least about 75% (e.g., from about 75% to about 100%) by weight olefins, and often they comprise at least about 85% (e.g., from about 85% to about 100% or from about 95% to about 100%) by weight olefins. In other embodiments, these amounts of olefins are representative of the total olefin percentages in the hydrocarbon feedstock itself, rather than the olefin percentages of the total hydrocarbons in the hydrocarbon feedstock. In yet further embodiments, these amounts of olefins are representative of the total percentage of two particular olefin reactants in the hydrocarbon feedstock, having differing carbon numbers, which can combine in the metathesis reactor or reaction zone to produce a third olefin having an intermediate carbon number (i.e., having a carbon number intermediate to that of (i) a first olefin (or first olefin reactant) and (ii) a second olefin (or second olefin reactant) having a carbon number of at least two greater than that of the first olefin).

As discussed above, aspects of the present invention are associated with the discovery of particular olefin reactant molar ratios, and ranges of these ratios, that provide a number of important benefits in olefin metathesis processes utilizing a catalyst comprising a tungsten hydride that is bonded to alumina present in the catalyst support. In particular, a first olefin (e.g., ethylene) and a second olefin (e.g., butylene) having a carbon number of at least two greater than that of the first olefin are present in the hydrocarbon feedstock such that the first olefin is at a stoichiometric deficit relative to the second olefin. In particular embodiments, for example, a molar ratio of the first olefin to the second olefin in the hydrocarbon feedstock is in a range from about 0.2:1 to less than 1:1, and is often in a range from about 0.4:1 to about 0.8:1.

In an exemplary embodiment, the two olefins (first and second olefins) of interest are ethylene (having two carbons) and butylene (having four carbons), which combine in the metathesis reactor or reaction zone to produce desired propylene (having three carbons). The term "butylene" is meant to encompass the various $C_4$ olefin isomers, namely butene-1, cis-butene-2, trans-butene-2, and isobutene. In the case of metathesis reactions involving butylene, it is preferred that the butylene in the hydrocarbon feedstock comprises predominantly (i.e., greater than about 50% by weight) butene-2 (both cis and trans isomers) and typically comprises at least about 85% (e.g., from about 85% to about 100%) butene-2, as butene-2 is generally more selectively converted, relative to butene-1 and isobutylene, to the desired product (e.g., propylene) in the metathesis reactor or reaction zone.

In many cases, however, the $C_4$ olefin isomer of interest is present in refinery or non-petroleum based process streams as a mixture that is at or near equilibrium with these other isomers. It may be advantageous to use such a mixture as the hydrocarbon feedstock (or combine such a mixture, as a hydrocarbon feedstock component, with a recycle stream, as discussed below, to provide the hydrocarbon feedstock), without separation or purification of any desired isomer(s). Otherwise, separation of a desired isomer (e.g., butene-2), upstream of the reactor or reaction zone, to a purity substantially in excess of its equilibrium concentration may be achieved using known techniques including distillation and adsorptive separation (including moving bed and simulated moving bed systems known in the art). In any such separation, generally a stream rich in isomers (e.g., butene-1 and isobutylene) other than the desired isomer (i.e., a stream containing either or both of these other isomers in a concentration in excess of equilibrium) is also produced. Subjecting this stream to isomerization to restore equilibrium or near equilibrium levels of isomers can then generate an additional amount of the desired isomer for contacting with the tungsten hydride/alumina catalyst, as described herein. For example, suitable isomerization catalysts and processes for restoring equilibrium concentrations of $C_4$ olefins in a mixture of butenes having a sub-equilibrium concentration of any particular $C_4$ olefin(s) are known in the art and include, for example, magnesium oxide containing isomerization catalysts as described in U.S. Pat. No. 4,217,244.

Integrated processes according to aspects of the invention therefore include separating, using a separation process (e.g., distillation or adsorptive separation), a desired $C_4$ olefin isomer (e.g., butene-1, butene-2, or isobutylene) from an impure mixture of this $C_4$ olefin isomer with other $C_4$ olefin isomers to provide a stream rich in the desired $C_4$ olefin isomer (i.e., having a concentration of butene-1, butene-2, or isobutylene above its equilibrium concentration with the other olefin isomers) and a stream lean in the desired $C_4$ olefin isomer (i.e., having a concentration of butene-1, butene-2, or isobutylene below its equilibrium concentration with the other olefin isomers). The hydrocarbon feedstock that is contacted with the tungsten hydride/alumina catalyst, according to this embodiment, comprises at least a portion of the stream rich in the desired $C_4$ olefin isomer. Optionally, the stream lean in the desired $C_4$ olefin isomer is then isomerized to provide an isomerization product comprising an additional amount of the desired $C_4$ olefin isomer, and this isomerization product may be recycled to the separation process to which the impure mixture, described above, is also fed.

In some cases, it may be desirable to increase the butene-2 content of butylene, for example to achieve the desired ranges discussed above, by subjecting butylene to isomerization to convert butene-1 and isobutylene, contained in the butylene, to additional butene-2. The isomerization may be performed in a reactor that is separate from (e.g., immediately upstream of) the reactor used for olefin metathesis. Alternatively, the isomerization may be performed in an isomerization reaction zone in the same reactor that contains an olefin metathesis reaction zone, for example by incorporating an isomerization catalyst upstream of the olefin metathesis catalyst or even by combining the two catalysts in a single catalyst bed. Suitable catalysts for carrying out the desired isomerization to increase the content of butene-2 in the butylene are known in the art and include, for example, magnesium oxide containing isomerization catalysts as described in U.S. Pat. No. 4,217,244.

As discussed above, the olefins may be derived from petroleum or non-petroleum sources. Crude oil refining operations yielding olefins, and particularly butylene, include hydrocarbon cracking processes carried out in the substantial absence of hydrogen, such as fluid catalytic cracking (FCC) and resid catalytic cracking (RCC). Olefins such as ethylene and butylene are recovered in enriched concentrations from known separations, including fractionation, of the total reactor effluents from these processes. Another significant source of ethylene is steam cracking, as discussed above. A stream enriched in ethylene is generally recovered from an ethylene/ethane splitter as a low boiling fraction, relative to the feed to the splitter, which fractionates at least some of the total effluent from the steam cracker and/or other ethylene containing streams. In the case of olefins derived from non-petroleum sources, both the ethylene and butylene, for example, may be obtained as products of an oxygenate to olefins conversion process, and particularly a methanol to light olefins conversion process. Such processes are known in the art, as discussed above, and optionally include additional conversion steps to increase the butylene yield such as by dimerization of ethylene and/or selective saturation of butadiene, as described in U.S. Pat. No. 7,568,018. According to various embodiments of the invention, therefore, at least a portion of the ethylene in the hydrocarbon feedstock is obtained from a low boiling fraction of an ethylene/ethane splitter and/or at least a portion of the butylene is obtained from an oxygenate to olefins conversion process.

In representative olefin metathesis processes, with an exemplary process being the metathesis of ethylene and butylene for the production of propylene, catalysts comprising a solid support and a tungsten hydride bonded to alumina present in the support, may be used to achieve economically favorable product yields under commercial process conditions. With respect to the first and second olefins (e.g., ethylene and butylene) that undergo metathesis, the per pass conversion level, based on the amount of carbon in these reactants that are converted to the desired product and byproducts (e.g., propylene and heavier, $C_5^+$ hydrocarbons), is generally at least about 30% by weight and typically from about 30% to about 65% by weight. Very favorable conversion levels, based on carbon, are achieved when the hydrocarbon feedstock comprises olefin reactants at molar ratios as described above. Due to the stoichiometric deficiency of the first, lower carbon number olefin reactant (e.g., ethylene) and stoichiometric excess of the second, higher carbon number olefin reactant (e.g., butylene), the conversion of the first olefin is greater than that of the second olefin, with the conversion of the first olefin typically exceeding the conversion of the second olefin by (i.e., the difference between the conversion of the first olefin and the conversion of the second olefin is) at least about 10% and often by at least about 20%. In representative embodiments, the per pass conversion of the first olefin (e.g., ethylene) is generally at least about 40% and is often in the range from about 60% to about 75%, while the per pass conversion of second, higher carbon number olefin (e.g., butylene) is generally at least about 25% and is often in the range from about 30% to about 50%.

In one or more separations (e.g., fractionation) of the reactor or reaction zone effluent downstream of the reactor or reaction zone where the hydrocarbon feedstock is contacted with the tungsten hydride/alumina catalyst, the desired product (e.g., propylene) may be recovered in substantially pure form by removing and recovering (I) unconverted olefins (e.g., ethylene and/or butylene) originally present in the hydrocarbon feedstock, and (II) other reaction products (e.g., one or more fractions comprising $C_5^+$ hydrocarbons including olefin oligomers and alkylbenzenes). Recycling of all or a portion of (I) back to the reactor or reaction zone may often be desirable for achieving complete or substantially complete overall conversion, or at least significantly higher overall conversion (e.g., from about 80% to about 100% by weight, or from about 95% to about 100% by weight) than the equilibrium-limited per pass conversion level. In other embodiments, it may be desirable to further separate, from (I), a fraction (Ia) rich in a desired $C_4$ olefin isomer (e.g., butene-2), relative to (I) and a fraction (Ib) lean in the desired $C_4$ olefin isomer, relative to (I), with streams (Ia) and (Ib) often having concentrations of the desired $C_4$ olefin isomer above and below, respectively, its equilibrium concentration with the other $C_4$ olefin isomers. In this case, all or a portion of (Ia) may be recycled directly back to the reactor or reaction zone, while all or a portion of (Ib) may be isomerized, as described above, to provide an isomerization product comprising an additional amount of the desired $C_4$ olefin isomer, and all or a portion of this isomerization product may be recycled to the reactor or reaction zone or otherwise to a separation process upstream of the reactor or reaction zone, as described above, to separate the desired $C_4$ olefin isomer (e.g., butene-2) in a purified form.

Downstream separation(s) of the olefin product(s) from the reactor or reaction zone effluent, in addition to those described above, are normally carried out to achieve a high purity of the desired product, particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted feedstock olefin components (e.g., ethylene and butylene) to the desired olefin(s) (e.g., propylene) having an intermediate carbon number is generally at least about 75% (e.g., in the range from about 75% to about 100%) by weight, typically at least about 80% (e.g., in the range from about 80% to about 100%) by weight, and often at least about 90% (e.g., in the range from about 95% to about 100%) by weight, based on the amount of carbon in the converted products. The per pass yield of the desired olefin product(s) is the product of the selectivity to this/these product(s) and the per pass conversion, which may be within the ranges discussed above. The overall yield, using separation and recycle of the unconverted olefin reactants as discussed above, can approach this/these product selectivity/selectivities, as essentially complete conversion is obtained (minus some purge and solution losses of feedstock and product(s), as well as losses due to downstream separation inefficiencies).

The conversion and selectivity values discussed above are achieved by contacting the hydrocarbon feedstock described above, either continuously or batchwise, with a catalyst as described herein comprising a solid support and a tungsten hydride bonded to alumina present in the support. Generally, the contacting is performed with the hydrocarbon feedstock being passed continuously through a fixed bed of the catalyst in an olefin metathesis reactor or reaction zone. For example, a swing bed system may be utilized, in which the flowing hydrocarbon feedstock is periodically re-routed to (i) bypass a bed of catalyst that has become spent or deactivated and (ii) contact a bed of fresh catalyst. A number of other suitable systems for carrying out the hydrocarbon feedstock/catalyst contacting are known in the art, with the optimal choice depending on the particular feedstock, rate of catalyst deactivation, and other factors. Such systems include moving bed systems (e.g., counter-current flow systems, radial flow systems, etc.) and fluidized bed systems, any of which may be integrated with continuous catalyst regeneration, as is known in the art.

As discussed above, the use of the tungsten hydride/alumina catalyst system, in combination with olefin reactant feed ratios where the first olefin is at a stoichiometric deficit relative to the second, higher carbon number olefin, results in significant performance benefits in terms of the catalyst activity, or level of conversion, based on total carbon in the olefin reactants, achieved at a given reaction temperature. Moreover, this increase in conversion level generally does not result in a loss in selectivity, as is normally observed, for example, when reaction severity is increased (e.g., by raising temperature, increasing residence time, and/or increasing reactant concentrations). Consequently, advantages in terms of desired product yields are obtained with the catalyst systems and process conditions described herein. Additional benefits are gained in terms of catalyst life or catalyst stability, resulting from the nature of the composition of the hydrocarbon feedstock.

Representative conditions for contacting of the hydrocarbon feedstock with the tungsten hydride/alumina catalyst, at which the above conversion and selectivity levels may be obtained, include a temperature from about 75° C. (167° F.) to about 250° C. (482° F.), and often from about 100° C. (212° F.) to about 200° C. (392° F.); an absolute pressure from about 0.1 bar (1.5 psi) to about 100 bar (1450 psi), and often from about 0.5 bar (7.3 psi) to about 35 bar (508 psi); and a weight hourly space velocity (WHSV) from about 1 hr$^{-1}$ to about 100 hr$^{-1}$, and often from about 5 hr$^{-1}$ to about 25 hr$^{-1}$. As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time. Under the olefin metathesis conditions described above, the hydrocarbon feedstock is normally partially or all in the vapor phase in the olefin metathesis reactor or reaction zone, but it may also be in the liquid phase, for example, in the case of heavier (higher carbon number) olefin feedstocks.

Importantly, the tungsten hydride/alumina catalysts according to embodiments of the invention and providing the significant benefits, as discussed above, comprise a tungsten hydride that is bonded to an oxygen atom of alumina present in the support. In general, the support comprises predominantly (i.e., at least 50% by weight) alumina, with the optional addition of other components such as other inorganic refractory metal oxides (e.g., silica, zirconia, titania, boria, thoria, ceria) and/or catalyst promoters or modifiers (e.g., alkali or alkaline earth metals, or transition metals in addition to tungsten). Typically, the support comprises alumina in an amount of at least about 90% (e.g., from about 90% to about 100%) by weight and often at least about 95% (e.g., from about 95% to about 100%) by weight.

The catalyst therefore comprises a support comprising alumina (aluminum oxide) to which a tungsten hydride is covalently bonded (grafted). The term "a tungsten hydride" refers to a tungsten compound that is supported on the catalyst. The tungsten atom of the tungsten compound is bonded to at least one hydrogen atom or hydrocarbon residue by at least one single, double, or triple bond. The tungsten atom is also bonded, through an oxygen linkage, to an aluminum atom of the alumina support. The tungsten hydride may be identified by one or more absorption bands, under infrared (IR) spectroscopy that are characteristic of a (W—H) bond, as described below. Otherwise, the tungsten hydride (W—H) bond may be detected with proton nuclear magnetic resonance (solid 1H-NMR) at 500 MHz, where the value of the tungsten hydride chemical shift $\delta_{W-H}$ is typically found at a value of about 10.6 parts per million (ppm) (e.g., in the range from about 10.3-10.9 ppm).

In representative supports, the alumina (aluminum oxide) is accessible to the tungsten hydride at the surface of the support. The support may be a relatively homogeneous composition comprising alumina throughout the mass of the support (e.g., from the core to the surface of the support). Alternatively, the support may be a relatively heterogeneous composition comprising alumina that is present, for example, only at a surface layer. In the latter case, the support may comprise aluminum oxide deposited, supported, or grafted onto an inorganic solid which may itself be an inorganic solid support, for example selected from metals, oxides, sulfides, and salts. Exemplary inorganic solids therefore include other inorganic refractory metal oxides besides alumina.

The support has a surface area generally within a range from 0.1 to 1000 m$^2$/g, and often from about 100 m$^2$/g to about 450 m$^2$/g. Surface area is measured according to the Brunauer, Emmett and Teller (BET) method based on nitrogen adsorption (ASTM D1993-03 (2008)). The support may comprise all or substantially all aluminum oxide, or it may be mixed with other support components, for example with more than 2% by weight of one or more other inorganic refractory metal oxides (e.g., silica). Also, the aluminum oxide of the support may be modified by one or more elements from groups 14 to 17 of the periodic table of the elements. The elements germanium and tin of group 14 are representative. For element group designations described herein, reference is made to the "CRC Handbook of Chemistry and Physics", 76$^{th}$ Edition (1995-1996), by David R. Lide, published by CRC Press, Inc. (USA), in which the groups of the periodic table are numbered 1 to 18.

The alumina of the support may be, for example, a porous alumina, non-porous alumina, a mesoporous alumina, or any mixture of two or all three of these aluminas. Porous aluminas are frequently referred to as "activated aluminas" or alternatively "transition aluminas." Porous aluminas are often partially hydroxylated and obtained by an "activation" treatment comprising heating and dehydration of a precursor selected from aluminum hydroxides (e.g., aluminum tri-hydroxides), hydroxides of aluminum oxide, or gel-form aluminum hydroxides. The activation treatment eliminates water present in the precursor, together with a proportionate amount of the hydroxyl groups, thereby leaving behind some residual hydroxyl groups and a specific porous structure. The surface of porous aluminas generally comprises a complex mixture of aluminum and oxygen atoms, as well as hydroxyl ions, all of which combine according to the specific crystalline form of the alumina and provide both acidic and basic sites. The alumina of the solid support may be a porous alumina selected from Y-alumina (gamma-alumina), η-alumina (eta-alumina), δ-alumina (delta-alumina), θ-alumina (theta alumina), K-alumina (kappa-alumina), ρ-alumina (rho-alumina) and X-alumina (chi-alumina), and preferably from among Y-alumina, δ-alumina, θ-alumina, and their mixtures. These various crystalline forms depend essentially on the selection of the precursor and the conditions of the activation treatment, in particular temperature and pressure. The activation treatment may be performed, for example, under a stream of air or another gas, such as an inert gas, at a temperature which may be within a range generally from 100° C. (212° F.) to 1000° C. (1832° F.), and typically from 200° C. (392° F.) to 1000° C. (1832° F.).

It is also possible to use porous or alternatively semi-porous aluminas, produced by an activation treatment as previously described, in particular comprising heating to a temperature from 500° C. (932° F.) to 1000° C. (1832° F.). These porous or semi-porous aluminas may comprise mixtures of porous aluminas in at least one of the previously described crystalline forms, such as Y-alumina, η-alumina, δ-alumina, θ-alumina, K-alumina, ρ-alumina or X-alumina, with a non-porous alumina (e.g., α-alumina), which may be present in the alumina in widely varying amounts (e.g., from 20% to 80% by weight). Porous aluminas are generally thermal decomposition products of aluminum tri-hydroxides, aluminum oxide hydroxides (or aluminum oxide hydrates), and gel-form aluminum hydroxides (or alumina gels). Aluminum tri-hydroxides of the general formula $Al(OH)_3 = Al_2O_3 \cdot 3H_2O$ may exist in various crystalline forms, such as gibbsite or hydrargillite (α-$Al(OH)_3$), bayerite (β-$Al(OH)_3$), or nordstrandite. Aluminum tri-hydroxides may be obtained by precipitation from aluminum salts in generally alkaline solutions. Aluminum oxide hydroxides of the general formula AlO(OH)=Al$_2$O$_3$.H$_2$O may also exist in various crystalline forms, such as diaspore (β-AlO(OH)) or boehmite (or α-AlO(OH)). Diaspore may be found in certain types of clay and bauxite, and may be synthesized by heat treatment of gibbsite at about 150° C. (302° F.) or by hydrothermal treatment of boehmite at about 380° C. (716° F.) under a pressure of about 500 bar (7250 psi). Boehmite may readily be obtained by heating the resultant gel-form precipitate with cold treatment of the aluminum salt solutions with ammonia. Aluminum oxide hydroxides may also be obtained by hydrolysis of aluminum alcoholates.

Gel-form aluminum hydroxides (or alumina gels) are generally aluminum polyhydroxides, in particular of the general formula: nAl(OH)$_3$.(n−1)H$_2$O, in which n is a number ranging from 1 to 8. Gel-form aluminum hydroxides may be obtained by one of the methods selected from among thermal decomposition of an aluminum salt, such as aluminum chloride, electrolysis of an aluminum salt, such as a mixture of aluminum sulfate and an alkali metal sulfate, hydrolysis of an aluminum alcoholate, such as aluminum methylate, precipitation from aluminates, such as an alkali metal or an alkaline-earth metal aluminate, and precipitation from an aluminum salt, for example by contacting an aqueous solution of Al$_2$(SO$_4$)$_3$ and ammonia, or of NaAlO$_2$ and an acid, or of NaAlO$_2$ and Al$_2$(SO$_4$)$_3$, after which the resultant precipitate may undergo aging and drying to remove water. Gel-form aluminum hydroxides generally assume the form of an amorphous alumina gel, and in particular the form of a pseudoboehmite.

Porous aluminas may have a specific surface area (BET) generally in a range from 50 m$^2$/g to 1000 m$^2$/g, typically from 75 m$^2$/g to 600 m$^2$/g, and often from 100 m$^2$/g to 450 m$^2$/g, with a range from 100 m$^2$/g to 250 m$^2$/g being exemplary. They may furthermore have a specific pore volume of generally at most 1 cm$^3$/g, typically at most 0.9 cm$^3$/g, and often at most 0.75 cm$^3$/g.

Non-porous aluminas include α-alumina (alpha-alumina), generally known as "calcined alumina" or "flame alumina" and existing in a natural state known as "corundum." They may in general be synthesized by a heat treatment, and in particular calcination, of a precursor selected from aluminum salts, aluminum oxide hydroxides, aluminum tri-hydroxides, and aluminum oxides, such as Y-alumina, at a temperature of greater than 1000° C. (1832° F.), and often greater than 1100° C. (2012° F.). Non-porous aluminas may contain impurities, such as other oxides, for example Fe$_2$O$_3$, SiO$_2$, TiO$_2$, CaO, Na$_2$O, K$_2$O, MgO, SrO, BaO and Li$_2$O, in proportions of less than 2% by weight, and often less than 1% by weight. They may have a specific surface area (BET) generally in a range from 0.1 m$^2$/g to less than 300 m$^2$/g, typically from 0.5 m$^2$/g to 300 m$^2$/g, and often from 0.5 m$^2$/g to 250 m$^2$/g. The support may also comprise a mesoporous alumina, for example having a surface area (BET) generally in the range of from 100 m$^2$/g to 800 m$^2$/g. Mesoporous aluminas generally have pores of an average width of from 2 nm to 0.05 μm.

As discussed above, the support may also comprise mixed aluminum oxides, or aluminum oxides combined with at least one other oxide in an amount generally from 2% to less than 80% by weight, typically from 2% to less than 50% by weight, and often from 2% to less than 40% by weight, with an amount from 2% to less than 30% by weight being exemplary. The other oxide(s) may be oxides of an element, M, selected from among metals of groups 1 to 13 and elements of group 14, with the exception of carbon, of the periodic table of the elements. More particularly, they may be oxides of an element M selected from alkali metals, alkaline-earth metals, transition metals and elements of groups 13 and 14, with the exception of carbon. Transition metals generally comprise the metals of groups 3 to 11, and often the elements 21 to 29, 39 to 47, 57 to 79 (including lanthanides) and actinides. The other oxide(s) are often oxides of an element M selected from transition metals of groups 3 to 7, lanthanides, actinides, and elements of groups 13 and 14, with the exception of carbon. More particularly, they may be selected from oxides of silicon, boron, gallium, germanium, titanium, zirconium, cerium, vanadium, niobium, tantalum, chromium, molybdenum, and tungsten.

The support may have a homogeneous composition throughout the entire mass of the support, or it may be heterogeneous and comprise, for example an aluminum oxide, mixed aluminum oxide, or modified aluminum oxide, as previously described, in the form of a surface layer of the support having a thickness that is less than a smallest dimension of the support, for example less than the diameter of a spherical support or less than the diameter of the circular cross section of a cylindrical support. In the case of a heterogeneous composition for the support, the core of the support (e.g., the portion that is not the surface layer) may comprise or consist of an inorganic solid selected from a metal, an oxide, a sulfide, and a salt. Inorganic refractory metal oxides are representative. The heterogeneous support may be prepared by dispersion, by precipitation, and/or by grafting of one of the precursors of aluminum oxide, as described above, onto the inorganic solid. Suitable precursors may include aluminum hydroxides, such as aluminum tri-hydroxides, aluminum oxide hydroxides, and gel-form aluminum hydroxides. Gel-form aluminum hydroxides (known as alumina gels or amorphous aluminas), as described previously, are preferred. A heterogeneous support may for example be produced by processing such a precursor by a sol-gel method or with the assistance of an organometallic compound that facilitates grafting onto the inorganic solid.

The catalyst, comprising a solid support comprising alumina, generally has the form of discreet particles of varying shapes and sizes. For example, the particles may have an average size of generally from 10 nm to 5 mm, and often from 20 μm to 4 mm The particles may assume their natural shape or may be shaped to have any of a number of forms, including a spherical, a spheroidal, a hemispherical, a hemispheroidal, a cylindrical or a cubic form, or the catalyst may assume the form of a rings, a tablet, a disc, or a pellet.

The catalyst essentially comprises a tungsten hydride that is grafted (covalently bonded) to alumina present in the support, generally by at least one single bond. The oxidation state of the tungsten hydride may have a value in a range from 2 to 6, and often from 4 to 6, which refers to the average oxidation state of tungsten atoms bonded to the alumina support. The tungsten hydride may furthermore be bonded to one or more atoms of hydrogen by single bonds (W—H) and optionally to one or more hydrocarbon residues, R, by single or multiple carbon-tungsten bonds. The number of hydrogen atoms bonded to an atom of tungsten depends on the oxidation state of tungsten, the number of single bonds between the tungsten atom and the support, and optionally the number of single or multiple bonds between the tungsten atom and a hydrocarbon residue, R. Thus, the number of hydrogen atoms bonded to a tungsten atom may be at least equal to 1 and at most equal to 5, and typically ranges from 1 to 4, and often from 1 to 3. Grafting or bonding of the tungsten hydride onto the solid support generally means that the tungsten atom is bonded by at least one single bond to alumina present in the support, and more particularly by at least one single bond (W—OAl) to at least one oxygen atom of the alumina. The number of single bonds between the tungsten atom and the alumina present in the support, in particular by a single bond (W—OAl), depends on the oxidation state of the tungsten and on the number of other bonds of the tungsten atom, and this number is generally 1, 2, or 3.

The tungsten atom of the tungsten hydride may optionally be bonded to one or more hydrocarbon residues, R, with one or more single, double, or triple carbon-tungsten bonds. The hydrocarbon residue(s), R, may be identical or different, saturated or unsaturated hydrocarbon residues, comprising, for example, generally from 1 to 20 and often from 1 to 10 carbon atoms. The hydrocarbon residues may optionally comprise silicon, as in the case of an organosilane residue. The hydrocarbon residues may be selected from (i) alkyl residues, such as linear or branched, aliphatic or alicyclic residues, for example alkyl, alkylidene or alkylidyne residues, having, for example, from 1 to 10 carbon atoms, (ii) aryl residues, having, for example, from 6 to 12 carbon atoms, and (iii) aralkyl, aralkylidene or aralkylidyne residues, for example, having from 7 to 14 carbon atoms.

The tungsten atom of the tungsten hydride, in addition to being bonded to alumina present in the catalyst support, may be bonded to the hydrocarbon residue, R, by one or more single, double, or triple carbon-tungsten bonds. The bond may be a single carbon-tungsten bond. In this case, the hydrocarbon residue, R, may be an alkyl residue, for example linear or branched, or an aryl residue, for example a phenyl residue, or an aralkylene residue, for example a benzyl residue, or a residue of the formula $(C_6H_5—CH_2—CH_2—)$. An alkyl residue is generally taken to mean a monovalent aliphatic residue obtained from the removal of a hydrogen atom from a carbon atom in a molecule of an alkane, an alkene, or an alkyne. In the particular case of the hydrocarbon residue, R, an alkyl residue also includes a monovalent aliphatic residue obtained from the removal of a hydrogen atom from a carbon atom in a molecule of an organosilane. Alkyl residues therefore include, for example, methyl ($CH_3$—), ethyl ($C_2H_5$—), propyl ($C_2H_5$—$CH_2$—), neopentyl (($CH_3$)$_3$C—$CH_2$—), allyl ($CH_2$=CH—$CH_2$—), alkynyl (R—C≡C—) (e.g., ethynyl (CH≡C—)), and neosilyl ($(CH_3)_3Si—CH_2$—) residues. The alkyl residue may be, for example, of the formula (R'$CH_2$—) where R' represents a linear or branched alkyl residue.

A double carbon-tungsten bond may also bond the tungsten hydride to the hydrocarbon residue, R. In this case, the hydrocarbon residue, R, may be an alkylidene residue, which may be linear or branched, or an aralkylidene residue. An alkylidene residue is generally a divalent aliphatic residue originating from the removal of two hydrogen atoms from the same carbon atom in the molecule of an alkane, or an alkene, or an alkyne, or even of an organosilane. Alkylidene residues therefore include, for example, methylidene ($CH_2$=), ethylidene ($CH_3CH$=), propylidene ($C_2H_5$—CH=), neopentylidene (($CH_3$)$_3$C—CH=), or allylidene ($CH_2$=CH—CH=) residue. The alkylidene residue may be, for example, of the formula (R'—CH=) where R' represents a linear or branched alkyl residue. An aralkylidene residue is generally taken to mean a divalent aliphatic residue originating from the removal of two hydrogen atoms from the same carbon in an alkyl, alkenyl or alkynyl residue bonded to an aromatic group.

A triple carbon-tungsten bond may also bond the tungsten hydride to the hydrocarbon residue, R. In this case, the hydrocarbon residue, R, may be an alkylidyne residue, which may be linear or branched, or an aralkylidyne residue. An alkylidyne residue is generally a trivalent aliphatic residue originating from the removal of three hydrogen atoms from the same carbon atom in the molecule of alkane, or an alkene, or an alkyne, or even of an organosilane, for example an ethylidyne ($CH_3$—C≡), propylidyne ($C_2H_5$—C≡), neopentylidyne (($CH_3$)$_3$C≡) or allylidyne ($CH_2$=CH≡) residue. The alkylidyne residue may be, for example, of the formula (R'—C≡), where R' represents a linear or branched alkyl residue. An aralkylidyne residue is generally a trivalent aliphatic residue originating from the removal of three atoms of hydrogen from the same carbon of an alkyl, alkenyl, or alkynyl residue bonded to an aromatic group.

Representative hydrocarbon residues, R, are selected from methyl, ethyl, n-propyl, isopropyl, n-butyl, isobutyl, neopentyl, allyl, neopentylidene, allylidene, neopentylidyne, and neosilyl.

The tungsten atom of the tungsten hydride that is grafted (bonded) to alumina present in the catalyst support may be complexed with one or more hydrocarbon ligands, for example aromatic or carbonyl ligands. A particular type of bonding of the tungsten hydride to alumina through a W—OAl linkage may be represented as follows:

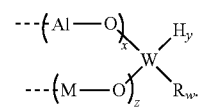

The tungsten hydride bonded to alumina of the support may therefore be represented by the above formula, wherein W, Al, O and H respectively represent atoms of tungsten, aluminum, oxygen and hydrogen, and M represents an atom of one or more elements of another oxide present in the support, as defined previously. R represents a hydrocarbon residue, as defined previously, and w, x, y, and z are integers, the sum of which (w+x+y+z) equals 2 to 6 (i.e., the oxidation state of the tungsten), wherein x=1 to 3, y=1 to 5, w=0 to 4 and z=0 to 2. The value of z is 0, for example, when the tungsten hydride is not bound, through an oxygen linkage, to a metal other than aluminum in the catalyst support. This condition occurs, for example, when the support comprises all or substantially all alumina. In the above formula, the —(Al—O) and -(M-O) bonds represent one or more single or multiple bonds, respectively, bonding the aluminum atom and the metal atom M to one of the atomic constituents of the support comprising alumina, and in particular to one of the oxygen atom constituents of this support.

Under infrared spectroscopy, the catalysts comprising a tungsten hydride, as described herein, generally exhibit one or more absorption bands which are characteristic of the (W—H) bond, the frequency of which bands may vary depending on the coordination sphere of the tungsten and particularly on the number of bonds of the tungsten with the support, with hydrocarbon residues R, and with other hydrogen atoms. Accordingly, at least two absorption bands have been found at 1903 cm$^{-1}$ and 1804 cm$^{-1}$, being characteristic of the (W—H) bond and in particular in the environment of the (W—OAl) bond, bonding the same tungsten atom of the tungsten hydride to an oxygen atom, which is in turn bonded to an aluminum atom of an α-alumina. By way of comparison, tungsten hydride grafted (bonded) under the same conditions onto a silica support generally exhibits under infrared spectroscopy at least one absorption band at 1940 cm$^{-1}$ or 1960 cm$^{-1}$, being characteristic of the (W—H) bond and in particular in the environment of the (W—OSi) bond, bonding the same tungsten atom of the tungsten hydride to an oxygen atom, which is in turn bonded to a silicon atom of the silica support.

The presence of a (W—H) bond of a tungsten hydride, which is bonded to alumina in the catalyst support, may also be detected using proton nuclear magnetic resonance (solid 1H-NMR) at 500 MHz, where the value of the tungsten hydride chemical shift $\delta_{W-H}$ is typically found at a value of about 10.6 parts per million (ppm) (e.g., in the range from about 10.3-10.9 µm).

In addition to a tungsten hydride, the catalyst may further comprise an aluminum hydride, for example at the surface of the support and/or in the vicinity of the grafted tungsten hydride. Without being bound by theory, it is believed that an aluminum hydride can be formed by opening of an aluminoxane bridge (of the formula Al—O—Al), which may be present at the surface of the support, and by reaction of the opened aluminoxane bridge and a hydrogen atom of a grafted tungsten hydride. A simple method for detecting the presence of aluminum hydride, in addition to tungsten hydride, in the catalyst involves performing a deuteration reaction of the catalyst. According to a particular method, the catalyst is subjected to a deuterium atmosphere under an absolute pressure of 66.7 kPa (10 psi) and a temperature generally from 25° C. (77° F.) to 80° C. (176° F.), and often about 60° C. (140° F.), for a period of about 15 minutes. Selective deuteration under these conditions replaces hydrogen atoms of the (W—H) bond with deuterium atoms, thereby forming (W-D) bonds which, under IR spectroscopy, have absorption bands at 1293 $cm^{-1}$ and 1393 $cm^{-1}$. Selective deuteration leaves the hydrogen atoms in the (Al—H) bonds unchanged, and these bonds may be identified under IR spectroscopy by an absorption band at 1914 $cm^{-1}$.

The solid supported catalyst, comprising a tungsten hydride grafted (bonded) to alumina present in the support, may be prepared by a method comprising dispersion and grafting of an organometallic tungsten precursor (Pr) onto a support comprising alumina. The tungsten in the precursor may be either bonded or otherwise complexed to at least one hydrocarbon ligand, so as to form a hydrocarbon compound or hydrocarbon complex, respectively, of tungsten grafted onto the support. Then, hydrogenolysis of the grafted hydrocarbon compound or hydrocarbon complex of tungsten, resulting from the previous dispersion and grafting, forms tungsten hydride grafted onto alumina of the support.

The organometallic tungsten precursor, Pr, may comprise a tungsten atom bonded to one or more hydrocarbon ligands. The tungsten atom may be bonded to a carbon of the hydrocarbon ligand by single, double or triple (carbon-tungsten) bonds. The hydrocarbon ligands may be identical or different, saturated or unsaturated hydrocarbon residues, for example aliphatic or alicyclic residues, generally having from 1 to 20 carbon atoms and often from about 1 to 10 carbon atoms. The hydrocarbon ligands may be selected from the hydrocarbon residues, R, described previously. The number of hydrocarbon ligands bonded to the tungsten atom depends on the oxidation state of tungsten in the precursor Pr and may be at most equal to this oxidation state. The number of hydrocarbon ligands may therefore be from 1 to 6, typically from 2 to 6, and often from 4 to 6.

The precursor, Pr, may also comprise a tungsten atom complexed to one or more hydrocarbon ligands, the oxidation state of the tungsten being in this case equal to zero. The hydrocarbon ligand may be selected from among aromatic ligands or carbonyl ligands. The precursor Pr may accordingly be selected from among bis-arene tungsten and hexacarbonyl tungsten.

Prior to dispersion and grafting of the organometallic precursor, the support comprising alumina may be subjected to calcination and/or dehydroxylation. Calcination of the support may be performed to oxidize any carbon optionally present in the support and thereby eliminate it as carbon dioxide. Calcination may involve subjecting the support to an oxidizing heat treatment, for example under a stream of dry air, at a temperature below the sintering temperature of the support. Suitable temperatures are generally from 100° C. (212° F.) to 1000° C. (1832° F.), and typically from 200° C. (392° F.) to 800° C. (1472° F.), for a duration sufficient to eliminate the carbon dioxide. The duration may range from 0.1 to 48 hours, and the calcination may be conducted at atmospheric pressure or otherwise under elevated pressure or subatmospheric pressure.

The support may also be subjected to dehydroxylation prior to dispersion and grafting of the organometallic precursor, Pr. Dehydroxylation may be performed to optionally eliminate residual water from the support, as well as a proportion of the hydroxyl groups. A residual quantity of hydroxyl groups is left behind, generally at the surface of the support, and optionally aluminoxane bridges (of the formula Al—O—Al) are formed. Dehydroxylation may be performed by subjecting the support to heat treatment under a stream of inert gas, for example under a stream of nitrogen, argon or helium, under a pressure which is preferably below atmospheric pressure, for example under an absolute pressure of from $10^{-4}$ Pa ($1.5 \times 10^{-8}$ psia) to $10^2$ kPa (14.5 psia), preferably from $10^{-2}$ Pa ($1.5 \times 10^{-6}$ psia) to 50 kPa (7.3 psia), at a temperature below the sintering temperature of the support, for example at a temperature generally from 100° C. (212° F.) to 1000° C. (1832° F.), and typically from 200° C. (392° F.) to 800° C. (1472° F.), and for a duration sufficient to leave behind an appropriate residual quantity of hydroxyl groups and/or aluminoxane bridges in the support. The duration may range from 0.1 to 48 hours. Also, the dehydroxylation step may advantageously be performed after the calcination step.

The dispersion and grafting or bonding of the organometallic precursor, Pr, may be performed by sublimation, by impregnation with the assistance of a solvent, or by dry mixing. In the case of sublimation, the precursor, Pr, which is generally in the solid state under normal conditions, is heated normally under subatmospheric pressure and at a temperature causing its sublimation and migration in the gaseous state onto the support. Sublimation may be performed at a temperature of from −30° C. (−22° F.) to 200° C. (392° F.), and at an absolute pressure from $10^{-4}$ Pa ($1.5 \times 10^{-8}$ psia) to 10 kPa (1.45 psia). Grafting of the precursor, Pr, onto the support may be monitored by IR spectroscopy. Any excess precursor Pr which has not grafted (bonded) onto the support may be removed by inverse sublimation.

The dispersion and grafting may also be performed by impregnation with the assistance of a solvent. In this case, the precursor, Pr, may be dissolved in a polar or non-polar organic solvent, for example pentane or ethyl ether. Impregnation may be performed by contacting the support comprising alumina with the impregnation solution of the precursor, Pr. Impregnation may be performed at a temperature of from −80° C. (−122° F.) to 200° C. (392° F.), under an inert atmosphere, for example an atmosphere of nitrogen, argon and/or helium, and preferably with stirring. In this manner, a suspension of a hydrocarbon compound or a complex of tungsten grafted onto the support is obtained. Any excess precursor Pr which has not grafted (bonded) onto the support may be removed by washing with an organic solvent, which may be identical to or different from that used during impregnation.

The dispersion and grafting may also be performed by dry mixing, including mechanical dry mixing in the absence of liquid or liquid solvent. In this case, the precursor, Pr, which is generally in the solid state under normal conditions, is mixed with the support comprising alumina in the absence of liquid or liquid solvent. Mechanical stirring under an inert atmosphere, for example an atmosphere of nitrogen, argon and/or helium, is used to form a mixture of two solids. During or after the dry mixing, heat and/or subatmospheric pressure may be used to cause migration of the precursor, Pr, and its reaction with and covalent bonding to the support. Any precursor that has not been grafted (bonded) onto the support may be removed by inverse sublimation or washing with organic solvent.

Production of the catalyst may further comprise hydrogenolysis, or reaction of the hydrocarbon compound, or alternatively the hydrocarbon complex, of tungsten grafted onto the support, as prepared in the manner described previously. The reaction is carried out to form a tungsten hydride grafted (bonded) onto the support. Hydrogenolysis is generally understood to mean a reaction involving cleavage of a molecule that accompanies bonding of hydrogen onto the two cleaved ends. Cleavage in this case occurs between the tungsten atom grafted onto the support and the carbon atom of a hydrocarbon ligand that is bonded to or otherwise complexed with the tungsten atom. Hydrogenolysis may be performed with the assistance of hydrogen or a reducing agent that is capable of converting the grafted hydrocarbon compound or hydrocarbon complex of tungsten into grafted tungsten hydride. Hydrogenolysis may be performed by contacting the grafted hydrocarbon compound or hydrocarbon complex of tungsten with the hydrogen or reducing agent. It may be performed under an atmosphere of hydrogen or an inert atmosphere when a reducing agent is used, using an absolute pressure of from $10^{-2}$ Pa ($1.5 \times 10^{-6}$ psia) to 10 MPa (145 psia), at a temperature of from 20° C. (68° F.) to 500° C. (932° F.) for a period of from 0.1 to 48 hours.

Overall aspects of the invention are directed to olefin metathesis processes that exploit the significant benefits found to be associated with the use of particular operating conditions and a particular catalyst system. More specifically, the combination of operating at a stoichiometric deficit of a first olefin reactant (e.g., ethylene) relative to a second, higher carbon number olefin reactant (e.g., butylene), together with a catalyst comprising a tungsten hydride bonded to alumina present in the catalyst support, provides important commercial advantages in terms of conversion and selectivity to desired product(s) having an intermediate carbon number. Further benefits include improved catalyst stability. Those having skill in the art, with the knowledge gained from the present disclosure, will recognize that various changes can be made in the above catalysts and olefin metathesis processes using the catalysts, without departing from the scope of the present disclosure.

The following examples are representative of the present invention and its associated advantages and are not to be construed as limiting the scope of the invention as set forth in the appended claims.

EXAMPLES 1-7

Varying Olefin Reactant Proportions in Olefin Metathesis with W—H/Al$_2$O$_1$ Catalysts A solid catalyst comprising a tungsten hydride grafted (bonded) to alumina was prepared as described in Example 3 of US 2007/0129584. The tungsten content of the catalyst was 5.5 wt-%, based on the total catalyst weight. The catalyst was evaluated for propylene production via olefin metathesis in a microreactor-scale experimental protocol. In particular, a hydrocarbon feedstock of an ethylene/butylene mixture was passed over a 135 mg sample loading of the catalyst at a temperature of 150° C. (302° F.) and a flow rate of about 20 Nml/min, corresponding to a weight hourly space velocity (WHSV) from about 10 hr$^{-1}$ to about 21 hr$^{-1}$. These conditions and 1 barg (15 psig) of reaction pressure were maintained over a testing duration of about 45 hours.

The reactor effluent composition was analyzed periodically by gas chromatography to determine the conversion level (per pass) of ethylene, butylene, and total carbon (i.e., percentage conversion, based on carbon present in the converted olefin reactants). The analytical results of the reactor effluent were also used to calculate the selectivity, based on the total percentage of converted carbon that resulted in the formation of propylene (propylene selectivity), C$_5$ olefins, and C$_6$ olefins.

Figure 8:
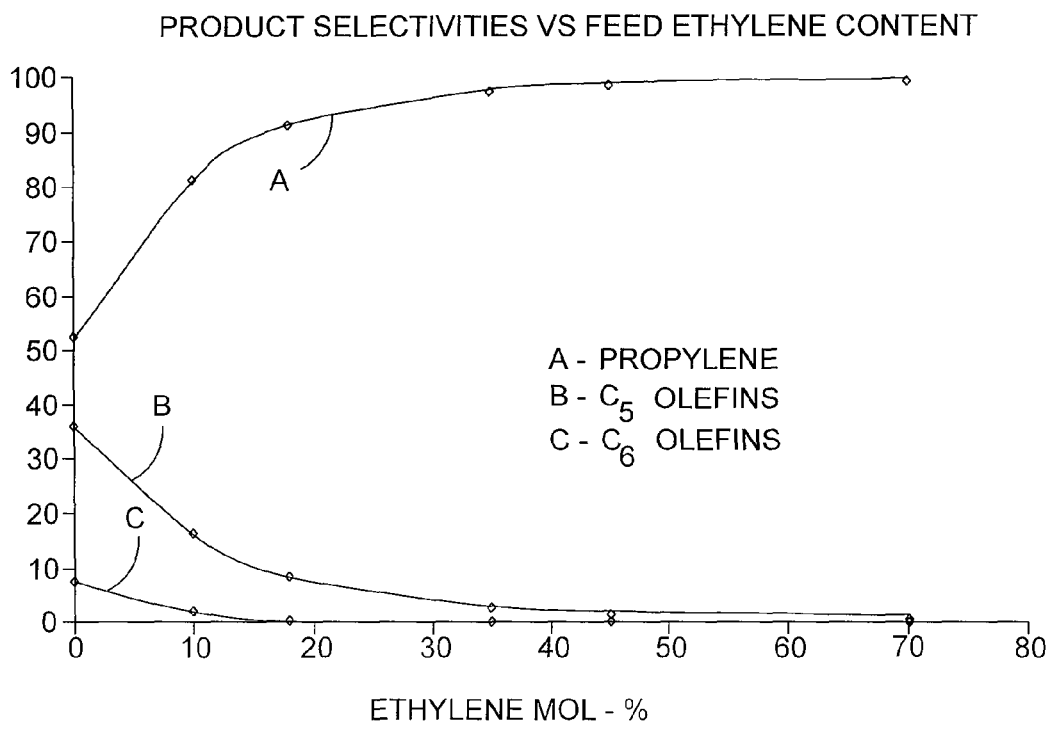
FIG. 8 is a graph showing the selectivity of the main product, propylene, as well as pentene (all $C_5$ olefins) and hexene (all $C_6$ olefins), as a function of ethylene content of the ethylene/butylene hydrocarbon feedstock. The selectivity data were obtained in the same experiments, used to test performance (conversion) at the different ethylene/butylene feed ratios, as described with respect to FIGS. 1-7.

A total of 7 tests were performed under the above conditions at varying proportions of the olefin reactants, ethylene and butylene, with a constant total hydrocarbon feedstock flow rate to the olefin metathesis reactor. Specifically, the catalyst performance was evaluated for feedstocks containing molar ethylene/butylene percentages of (1) 0%/100%, (2) 10%/90%, (3) 18%/82%, (4) 35%/65%, (5) 45%/55%, (6) 70%/30%, and (7) 100%/0%. The individual olefin reactant and total carbon conversion levels as a function of time on stream are shown in FIGS. 1-7. The data illustrate that total carbon conversion increases as the ethylene concentration increases, but reaches a maximum at about 35 mol-% ethylene, corresponding to an ethylene/butylene molar ratio of about 0.54:1. The most efficient utilization of carbon in the feedstock was therefore found to deviate significantly from the theoretical 1:1 molar ratio, based on reaction stoichiometry (1 mole of ethylene+1 mole of butylene→2 moles of propylene). Moreover, FIG. 8 illustrates that propylene selectivity observed at the 35 mol-% ethylene in the feed, corresponding to the highest feedstock carbon conversion level, is near the maximum value and desirably on the "flat" portion of the selectivity vs. mol-% ethylene curve.

Thus, propylene selectivity is not compromised by operating in this region of high feedstock carbon conversion, and in particular at a stoichiometric deficit of ethylene. Furthermore, the catalyst stability is relatively high in this operating region, which is apparent when comparing the conversion level decline, over the testing duration, for the 35 mol-% ethylene feedstock relative to, for example, the much higher rate of decline for the 100 mol-% ethylene feedstock.

The invention claimed is:

1. An olefin metathesis process comprising:
   contacting a hydrocarbon feedstock with a catalyst comprising a solid support and a tungsten hydride bonded to alumina present in the support,
   wherein the hydrocarbon feedstock comprises olefins including a first olefin and a second olefin having a carbon number of at least two greater than that of the first olefin, to produce a third olefin having an intermediate carbon number, and wherein a molar ratio of the first olefin to the second olefin in the hydrocarbon feedstock is from about 0.2:1 to less than 0.5:1.

2. The process of claim 1, wherein the catalyst comprises tungsten in an amount from about 1% to about 10% by weight.

3. The catalyst of claim 1, wherein the support comprises alumina in an amount of at least about 95% by weight.

4. The catalyst of claim 1, wherein the support has a BET surface area from about 100 m$^2$/g to about 450 m$^2$/g based on nitrogen adsorption.

5. The catalyst of claim 1, wherein the average oxidation state of tungsten in the tungsten hydride is from 4 to 6.

6. The process of claim 1, wherein the first olefin and the second olefin are converted to the third olefin with a selectivity of at least about 80% based on carbon.

7. The process of claim 6, wherein the first olefin and the second olefin are converted to the third olefin with a selectivity from about 95% to about 100% based on carbon.

8. The process of claim 6, wherein a per pass conversion of the first olefin is at least about 40%.

9. The process of claim 1, wherein the hydrocarbon feedstock comprises at least about 85% by weight olefins.

10. The process of claim 1, wherein the conversion of the first olefin exceeds the conversion of the second olefin by at least about 10%.

11. The process of claim 1, wherein the hydrocarbon feedstock is contacted with the catalyst at a temperature from about 75° C. (167° F.) to about 250° C. (482° F.), an absolute pressure from about 0.5 bar (7.3 psi) to about 35 bar (508 psi), and a weight hourly space velocity from about 1 $hr^{-1}$ to about 100 $hr^{-1}$.

12. The process of claim 1, wherein the first olefin is ethylene, the second olefin is butylene, and the third olefin is propylene.

13. The process of claim 12, wherein at least a portion of the ethylene is obtained from a low boiling fraction of an ethylene/ethane splitter.

14. The process of claim 12, wherein at least a portion of the butylene is obtained from an oxygenate to olefins conversion process or a fluid catalytic cracking process.

15. The process of claim 12, wherein the ethylene and the butylene are converted to propylene at a per pass conversion of at least about 30% based on carbon.

16. The process of claim 15, wherein the ethylene and the butylene are converted to propylene with a selectivity of at least about 80% based on carbon.

17. The process of claim 15, wherein the ethylene and the butylene are converted to propylene with a selectivity from about 95% to about 100% based on carbon.

18. The process of claim 12, wherein the conversion of ethylene exceeds the conversion of butylene by at least about 10%.

19. A process for producing propylene from the metathesis of ethylene and butylene, the process comprising contacting a hydrocarbon feedstock comprising predominantly ethylene and butylene at an ethylene : butylene molar ratio from about 0.2:1 to less than 0.5:1 with a catalyst comprising a solid support and a tungsten hydride bonded to alumina present in the support, wherein the conversion of ethylene exceeds the conversion of butylene by at least about 10%, and wherein the ethylene and the butylene are converted to propylene with a selectivity of at least about 95% based on carbon.

* * * * *